(12) United States Patent
Diaz Jimenez

(10) Patent No.: US 8,474,450 B2
(45) Date of Patent: Jul. 2, 2013

(54) ENHANCEMENTS INTRODUCED INTO PROLONGED TRACHEAL CANNULATION PROCESSES

(76) Inventor: Jose Pablo Diaz Jimenez, Sitges (ES)

( * ) Notice: Subject to any disclaimer, the term of this patent is extended or adjusted under 35 U.S.C. 154(b) by 739 days.

(21) Appl. No.: 12/616,953

(22) Filed: Nov. 12, 2009

(65) Prior Publication Data

US 2011/0108037 A1    May 12, 2011

(51) Int. Cl.
*A61M 11/00*    (2006.01)
(52) U.S. Cl.
USPC ............ 128/200.26; 128/207.14; 128/207.15
(58) Field of Classification Search
USPC ........................... 128/200.26, 207.14, 207.15
See application file for complete search history.

(56) References Cited

U.S. PATENT DOCUMENTS

| | | | | |
|---|---|---|---|---|
| 3,606,669 A * | 9/1971 | Kemble | ........................... | 29/434 |
| 3,721,233 A * | 3/1973 | Montgomery et al. | .. | 128/207.14 |
| 4,003,381 A * | 1/1977 | Gilbert | ...................... | 128/207.29 |
| 4,449,523 A * | 5/1984 | Szachowicz et al. | ..... | 128/200.26 |
| 4,465,068 A * | 8/1984 | Cantu | ................ | 606/1 |
| 4,794,924 A * | 1/1989 | Eliachar | .................... | 128/207.16 |
| 5,056,515 A * | 10/1991 | Abel | ....................... | 128/207.15 |
| 5,107,828 A * | 4/1992 | Koss et al. | .............. | 128/200.26 |
| 5,771,888 A * | 6/1998 | Keim | ....................... | 128/207.15 |
| 7,341,061 B2 * | 3/2008 | Wood | ....................... | 128/207.29 |
| 7,631,642 B2 * | 12/2009 | Freitag et al. | ............ | 128/200.26 |
| 7,987,851 B2 * | 8/2011 | Blom et al. | .............. | 128/207.16 |

\* cited by examiner

*Primary Examiner* — Steven Douglas
(74) *Attorney, Agent, or Firm* — Michael J. Striker

(57) ABSTRACT

A method for positioning a cannula for permanent implant through the orifice or tracheostoma in a fully aligned manner with the help of an inserter. The inner end or suprastomal extension of the cannula, upon withdrawing the inserter is vertically positioned in the supra-ostial area of the trachea, allowing, once the permanent cannula has been permanently positioned, the introduction of a perforated cannula having a characteristic curvature therethrough. The perforated cannula is oriented, through the lower aperture of the permanent cannula -1-, towards the interior of the lungs in order to allow insufflation of air from the exterior, while the exhaled air is derived through the vertical extension towards the larynx through the orifices disposed in the curvature elbow thereof.

3 Claims, 1 Drawing Sheet

ENHANCEMENTS INTRODUCED INTO PROLONGED TRACHEAL CANNULATION PROCESSES

The object of the present invention are enhancements introduced into current medical-surgical and emergency medicine action systems for carrying out prolonged tracheal cannulation in the throat area, in patients wherein the prevention of granulomas in said type of action is essential or necessary, enhancements which are described in detail below.

STATE OF THE ART

The processes currently used in prolonged tracheal cannulation in the throat area do not offer full guarantee of protection of the inner walls of the tracheal area where the intervention is carried out, on not having the necessary auxiliary or complementary elements to prevent the traditionally used perforated silver cannula from coming into contact with the delicate tissue of said tracheal area.

DESCRIPTION OF THE INVENTION

The prolonged cannulation process system of the invention is based on the adoption of a set of three elements to be used by the doctor who will be carrying out the intervention, which are described below:

- A silicone cannula for permanent implant through the tracheostoma having, as a characteristic and differentiating element, a suprastomal extension that ensures permeability of the laryngotracheal tube to the rest of the trachea.
- A inserter and rectifier of the aforementioned cannula allowing alignment thereof on being introduced through the tracheostoma until coming into contact with the rear wall of the trachea, said inserter allowing, on being withdrawn, the upper part of the cannula to remain introduced and favourably positioned in the supra-ostial area of said part of the trachea.
- A traditional perforated cannula, made of silver or a material that is biocompatible with polyvinyl chloride which, when introduced through the interior of the permanent cannula mentioned in the preceding paragraphs, is adequately positioned without damaging or injuring the stoma, as it is protected by the repeatedly mentioned cannula for permanent implant during introduction thereof.

GRAPHICAL INFORMATION

This description is accompanied by a set of drawings wherein, by way of practical and non-limiting example, the three previously detailed components are firstly represented, followed by the details of the action process for positioning the perforated cannula.

In said drawings.

DETAILED DESCRIPTION OF THE INVENTION

The enhancements of the invention are based on the use of a cannula for permanent implant -1-, made of silicone, having on its outer front part a fixing strip -2- with an angular folding, the vertex whereof, disposed on the lower part, has an aperture -3-, while the inner end has a suprastomal extension disposed in a substantially vertical position -4-, ending in a bevel-cut aperture -5-. This vertical extension -4- of the inner end ensures permeability of the laryngotracheal tube to the rest of the trachea.

The inserter -6- consists of a cylindrical bolt and rounded inner end -6a-, while its other end, also rounded, has a ring-shaped projection -7- with rounded edges.

Figure 1:
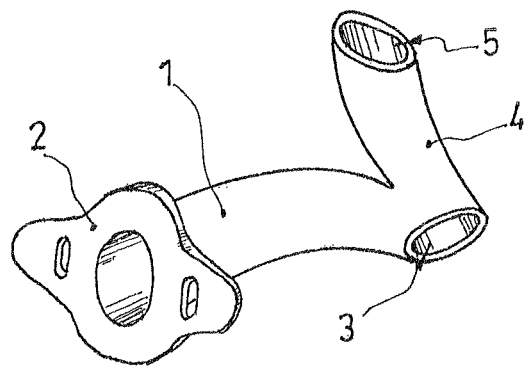
FIG. 1 shows a perspective view of the silicone cannula for permanent implant.
Figure 2:
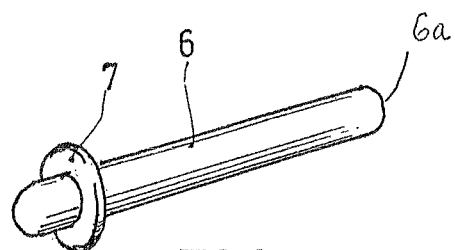
FIG. 2 shows a perspective view of the inserter.
Figure 3:
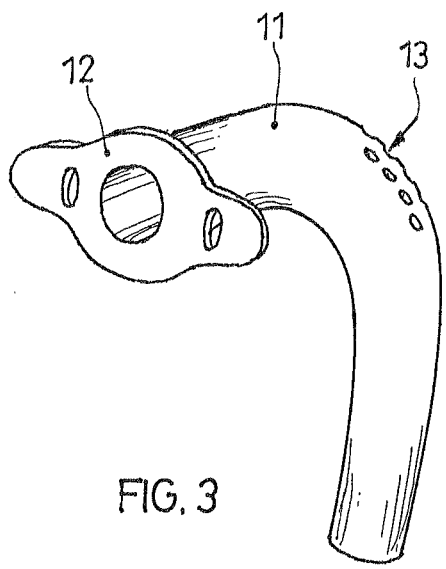
FIG. 3 shows a perspective view of the perforated silver cannula.
Figure 4:
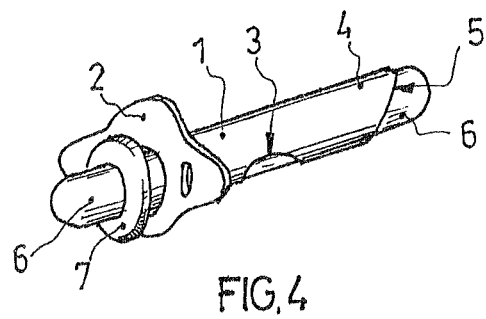
FIG. 4 shows the permanent cannula with the inserter positioned in its interior and having adopted the practical shape required for being introduced through the tracheostoma.

Said inserter -6- is introduced into the interior of the permanent cannula -1- so as to align it and obtain the optimal introduction position of the cannula inside the trachea -8-, as shown in FIG. 4, where the ring-shaped projection -7- limits the excessive introduction of the inserter -6- inside the permanent cannula -1-. This cannula -1- is longitudinally aligned, including its vertical inner end -4-, thereby favouring the introduction of the cannula-inserter assembly inside the trachea -8- through the aperture or tracheostoma -9-, until coming into contact with the rear wall of the trachea.

Figure 5:
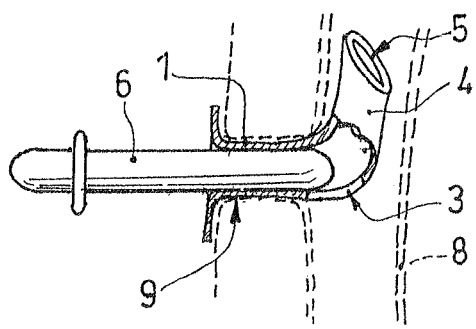
FIG. 5 shows the permanent cannula positioned inside the trachea while the inserter is being withdrawn.
Figure 6:
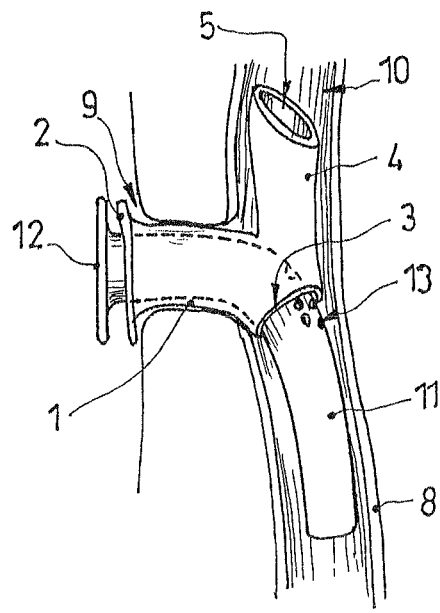
FIG. 6 finally shows the final position of the perforated cannula inside the permanent cannula, both positioned inside the trachea for carrying out the desired function through the intervention.

On withdrawing the inserter -6- while continuing to introduce the permanent cannula -1- towards the interior, as shown in FIG. 5, the vertical inner end -4- thereof, due to the flexibility of the material, is spontaneously folded upwards so as to become introduced into the supra-ostial portion -10- of the trachea -8-. The bevelled cut -5- of that outer part -4- of the permanent cannula -1- avoids injury due to contact with the rear wall of said supra-ostial portion -10- of the trachea -8-, area where the larynx and vocal chords are found.

The perforated cannula -11-, made of silver or a material that is biocompatible with polyvinyl chloride and of classic shape and characteristics, has a curved shape with a front strip -12- for adequate fixing thereof and orifices -13- in its curvature elbow.

Said perforated cannula -11- is introduced through the interior of the permanent cannula -1-, disposing the curvature towards the interior and downwards, towards the lungs, in the usual manner, through the aperture -3- disposed in the central part of said permanent cannula -1-, being thus positioned so that the air insufflated from the exterior is directed towards the lungs through the lower part of the trachea -8-, while the air exhaled towards the larynx through the vertical inner end -4- of the permanent cannula -1- passes through the orifices -13-. This allows phonation by the patient on allowing and ensuring transmission of the air exhaled towards the larynx.

Manipulation of this perforated cannula -11- through the interior of the permanent cannula -1- does not injure the tracheostoma -9-, as it is protected by the aforementioned permanent cannula -1-.

In this manner, the jointly disposed permanent cannula -1- and perforated cannula -11- may be conventionally fixed to the contour of the patient's throat.

Having sufficiently described the essentiality of the enhancements that are the object of the present invention, we must indicate that it will not be altered by variations in the design or type of material used in the practical embodiment of the three previously described components, summarising this essentiality in the following claims.

The invention claimed is:

1. A method for positioning a cannula in prolonged tracheal cannulation processes in which the cannula is permanently implanted through a tracheostoma, comprising the following steps:
providing a permanent cannula for permanent implant, said cannula having an outer end in the form of a substantially vertical suprastomal extension in an inner part ending in a bevel-cut aperture and an aperture terminating on a vortex of a lower part, said cannula further having a inserter in the form of a cylindrical bolt with rounded ends and a ring-shaped projection that limits introduction thereof into the permanent cannula, wherein the inserter is disposed inside the permanent cannula;
aligning and maintaining said permanent cannula in a longitudinal position in order to facilitate introduction thereof into the trachea through the tracheostoma;
withdrawing the inserter once the permanent cannula is thus disposed.

2. The method according to claim 1, further comprising the steps of spontaneously positioning, folding upwards, the outer end of the permanent cannula on withdrawing the inserter, becoming introduced into the supra-ostial area of the trachea, wherein said beveled cut of the end aperture prevents, whereby the permanent cannula for implant is permanently positioned for introduction of a perforated cannula.

3. An improvement in prolonged tracheal cannulation processes, wherein a permanent cannula for permanent implant is previously disposed in an aperture or tracheostoma, wherein a perforated cannula is introduced through said permanent cannula, wherein said perforated cannula is made of silver or a material that is biocompatible with polyvinyl chloride and has a curved shape, wherein said perforated cannula is introduced through the permanent cannula with its curvature facing downward towards lungs of a patient undergoing said cannulation process, through an aperture of a lower part of the permanent cannula, wherein said perforated cannula is positioned to permit passage of insufflated air towards the lungs while allowing, through orifices disposed in a curvature elbow thereof, the transmission of exhaled air towards the larynx of said patient through a vertical inner end of the permanent cannula, thereby allowing phonation.

* * * * *